United States Patent [19]

Huynh-Ba et al.

[11] Patent Number: 5,252,252

[45] Date of Patent: Oct. 12, 1993

[54] ANISOTROPIC COMPOUNDS AND LIQUID CRYSTAL MIXTURES

[75] Inventors: Tuong Huynh-Ba, Pully; Maged A. Osman, Zurich, both of Switzerland

[73] Assignee: Merck Patent Gesellschaft mit beschraenkter Haftung, Darmstadt, Fed. Rep. of Germany

[21] Appl. No.: 883,432

[22] Filed: May 15, 1992

Related U.S. Application Data

[60] Division of Ser. No. 333,769, Apr. 6, 1989, Pat. No. 5,120,467, which is a continuation-in-part of Ser. No. 917,138, Oct. 9, 1986, abandoned, which is a division of Ser. No. 648,431, Sep. 10, 1984, Pat. No. 4,723,005.

[30] Foreign Application Priority Data

Sep. 10, 1983 [DE] Fed. Rep. of Germany ....... 3332692

[51] Int. Cl.$^5$ ................. C09K 19/06; C09K 19/34; C09K 19/30; C09K 19/12
[52] U.S. Cl. ................ 252/299.6; 252/299.61; 252/299.63; 252/299.66; 252/299.67; 252/299.01
[58] Field of Search ............. 252/299.61, 299.63, 252/299.66, 299.67, 299.6, 299.01

[56] References Cited

U.S. PATENT DOCUMENTS 3,951,846  4/1976  Gavrilovic ............. 252/299.65

(List continued on next page.)

FOREIGN PATENT DOCUMENTS

| | | |
|---|---|---|
| 0047877 | 3/1982 | European Pat. Off. |
| 0058981 | 9/1982 | European Pat. Off. |
| 0159872 | 10/1985 | European Pat. Off. |
| 0174816 | 3/1986 | European Pat. Off. |
| 0191600 | 8/1986 | European Pat. Off. |
| 0225195 | 6/1987 | European Pat. Off. |
| 2544577 | 5/1976 | Fed. Rep. of Germany |
| 3302218 | 8/1983 | Fed. Rep. of Germany |
| 2010271 | 2/1970 | France |
| 0155063 | 5/1982 | German Democratic Rep. |
| 57-50933 | 3/1982 | Japan |
| 57-54137 | 3/1982 | Japan |
| 57-99542 | 6/1982 | Japan |
| 57-108056 | 7/1982 | Japan |
| 1596011 | 8/1981 | United Kingdom |
| 1249492 | 10/1981 | United Kingdom |
| 2092169 | 8/1982 | United Kingdom |
| 2111993 | 7/1983 | United Kingdom |

OTHER PUBLICATIONS

Petrzilka, Mol. Cryst. Liq. Cryst., vol. 111, pp. 329-346 (Nov. 1984) (Presented at the 13th Freuburger Arbeitstagung Flussigkristalle, Frieburg, Germany, Mar. 23-25, 1983.

Demus et al., Flüssige Kristalle in Tabellen II, veb Deutscher Verlag für Grundstoffihoustrie, Leipzig, p. 38, Nos. 5233-5238 (1984), Compounds published by Deutscher, H.-J., Dissertation B, Halle 1980.

Abstract presented at 13th Freiburger Arbeitstagung

*Primary Examiner*—Robert L. Stoll
*Assistant Examiner*—C. Harris
*Attorney, Agent, or Firm*—Millen, White, Zelano & Branigan

[57] ABSTRACT

New anisotropic compounds of the formula (1) are useful in liquid crystal mixtures for electrooptical displays; at least one of the end groups of the compounds (1) is an alkyl group which carries cyano or halogen in a terminal or non-terminal position. This offers advantages for longitudinal polarization and/or cross-polarization of the anisotropic compounds with the aid of the comparatively highly polarizing cyano or halogen substituents, in particular high clear points, low $$\frac{\Delta\epsilon}{\epsilon_\perp}$$

values and/or negative $\Delta\epsilon$ values.

16 Claims, No Drawings

U.S. PATENT DOCUMENTS

| | | | |
|---|---|---|---|
| 3,983,049 | 9/1976 | Aftergut et al. | 252/299.5 |
| 4,027,950 | 6/1977 | Moriyama et al. | 252/299.5 |
| 4,147,655 | 4/1979 | Dubois et al. | 252/299.67 |
| 4,191,776 | 3/1980 | Nicki et al. | 560/11 |
| 4,285,829 | 8/1981 | Eidenschink et al. | 252/299.63 |
| 4,293,424 | 10/1981 | Deutscher et al. | 252/299.63 |
| 4,311,610 | 1/1982 | Zaschke et al. | 252/299.61 |
| 4,330,426 | 5/1982 | Eidenschink et al. | 252/299.63 |
| 4,344,856 | 8/1982 | Demus et al. | 252/299.61 |
| 4,348,224 | 9/1982 | Demus et al. | 252/299.61 |
| 4,361,494 | 11/1982 | Osman et al. | 252/299.63 |
| 4,363,767 | 12/1982 | Demus et al. | 558/273 |
| 4,393,231 | 7/1983 | Misaki et al. | 252/299.67 |
| 4,400,293 | 8/1983 | Romer et al. | 252/299.63 |
| 4,510,069 | 4/1985 | Eidenschink et al. | 252/299.61 |
| 4,514,317 | 4/1985 | Huynh-ba et al. | 252/299.62 |
| 4,550,981 | 11/1985 | Petrzilka et al. | 252/299.63 |
| 4,564,694 | 1/1986 | Hirai et al. | 560/1 |
| 4,565,425 | 1/1986 | Petrzilka et al. | 359/103 X |
| 4,572,794 | 2/1986 | Eidenschink et al. | 252/299.63 |
| 4,576,732 | 3/1986 | Isogai et al. | 252/299.67 |
| 4,583,826 | 4/1986 | Petrzilka et al. | 359/103 X |
| 4,592,858 | 6/1986 | Higuchi et al. | 252/299.66 |
| 4,596,667 | 6/1986 | Inukai et al. | 252/299.67 |
| 4,613,209 | 9/1986 | Goodby et al. | 252/299.67 |
| 4,622,163 | 11/1986 | Huynh-ba et al. | 252/299.63 |
| 4,657,695 | 4/1987 | Saito et al. | 252/299.61 |
| 4,668,427 | 5/1987 | Saito et al. | 252/299.6 |
| 4,694,098 | 9/1987 | Hirai et al. | 252/299.63 |
| 4,695,650 | 9/1987 | Walba et al. | 252/299.67 |
| 4,695,651 | 9/1987 | Higuchi et al. | 252/299.62 |
| 4,725,688 | 2/1988 | Taguchi et al. | 252/299.61 |
| 5,120,467 | 6/1992 | Huynh-ba et al. | 252/299.61 |

OTHER PUBLICATIONS

Fluessigkristalle, Freiburg i. Br., Ger., Mar. 23–25, 1983 (Petrzilka).

Tsuno et al., Bull. Chem. Soc. Jpn., vol. 51(2), pp. 596–600 (1978).

Goodby et al., Liquid Crystals and Ordered Fluids, vol. 4, Griffin et al. eds., Plennum Press, N.Y., pp. 1–22 (1984), Proceedings of an ACS Symposium, Las Vegas, Mar. 29–Apr. 1, 1982.

Dabrowski et al., Mol. Cryst., Liq. Cryst., vol. 87, pp. 109–135 (Jun. 1982).

Demus et al., Mol. Cryst. Liq. Cryst., vol. 63, pp. 129–144 (1981).

Titov et al., Mol. Cryst. Liq. Cryst., vol. 47, pp. 1–5.

Dabrowski et al., Mol. Cryst. Liq. Cryst., vol. 107, pp. 411–43 (Jun. 1984).

Demus, Nonemissive Electrooptic Displays, pp. 83–119 (1975).

ANISOTROPIC COMPOUNDS AND LIQUID CRYSTAL MIXTURES

This application is a divisional application of U.S. Ser. No. 07/333,769 of Apr. 6, 1989, U.S. Pat. No. 5,120,467 which is a continuation-in-part of Ser. No. 06/917,138 of Oct. 9, 1986, abandoned, which is a divisional application of Ser. No. 06/648,431 of Sep. 10, 1984, now U.S. Pat. No. 4,723,005.

The invention relates to new anisotropic compounds for use in liquid crystal mixtures (LC mixtures) for electrooptical displays. The invention also relates to LC mixtures containing the new anisotropic compounds.

As is known, anisotropic compounds, the molecules of which carry, for polarization in the direction of the longitudinal axis of the molecule and/or at right angles thereto, certain substituents which effect this polarization, are required for the operation of various types of electrooptical displays. The polarization effect thereby caused is manifested by the positive or negative anisotropy of the dielectric constant (DCA or $\Delta\epsilon$) measured parallel ($\epsilon_{\parallel}$) and perpendicularly ($\epsilon_{\perp}$) to the molecular axis, where $\Delta\epsilon = \epsilon_{\parallel} - \epsilon_{\perp}$.

Virtually all the known anisotropic compounds for liquid crystal mixtures contain two to four cyclic radicals which are linked with one another by bridge members (covalent bonds or particular divalent groups), and in most cases also carry so-called end groups, according to the general formula I

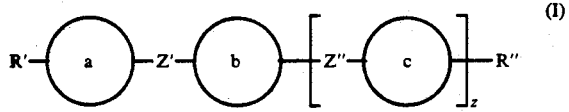

in which R' and R'' are the end groups, a, b and c are the cyclic radicals and Z' and Z'' are the bridge members; z is 0, 1 or 2.

In a typical case, polarization in the direction of the longitudinal axis of the molecule—called longitudinal polarization for short below—and accordingly the contribution to $\epsilon_{\parallel}$ is effected by a highly polarizing terminal group, such as the cyano group, on one end of the molecule (as R' or R'') and an alkyl or alkoxy group on the other end of the molecule (R'' or R').

The polarization at right angles to the longitudinal axis of the molecule—called cross-polarization for short below—is generally effected by polarizing substituents in the "lateral" position, and in particular hitherto virtually always by substituents on rings, such as cyano or halogen atoms, usually fluorine or chlorine, on the aromatic cyclic radicals, usually benzene rings, in accordance with the formula II

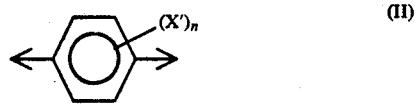

in which X' is the polarizing group, n is 1 or 2 and the arrows approximately correspond to the longitudinal axis of the molecule.

Formula II shows unambiguously that this customary type of cross-polarization with the aim of increasing $\epsilon_{\perp}$, for example for anisotropic substances with an overall negative DCA or for anisotropic substances with a positive DCA and at the same time by use of the smallest possible values of the ratio $$\frac{\Delta\epsilon}{\epsilon_{\perp}},$$

unavoidably leads to a considerable widening of the molecule, which is a disadvantage because it leads to a reduction in the clear point, and may result in other disadvantages. The limitation of the cross-polarization according to formula II to the presence of at least one aromatic ring in the molecule can also have an adverse effect.

The desirability of anisotropic compounds with a positive DCA and as small as possible values of $$\frac{\Delta\epsilon}{\epsilon_{\perp}}$$

is illustrated, for example, in commonly assigned European Application No. 79,200,259.4, and is achieved there by combination of longitudinal polarization and cross-polarization with substituents on rings.

However, problems also result in longitudinal polarization without cross-polarization of the molecule if a highly polarizing substituent must be attached to a cycloaliphatic radical. As is known, the replacement of the aromatic rings by cycloaliphatic radicals often offers various advantages, such as lower viscosity and reduced optical anisotropy; however, it is found that substituents on the rings, such as cyano groups on cycloaliphatic radicals, lead to a reduction in the clear point or can even effect disappearance of the mesophase, especially if O or N is at the same time bonded directly to the cycloaliphatic radical. Thus, for example, cyclohexyl derivatives with a terminal nitrile group, according to formula III

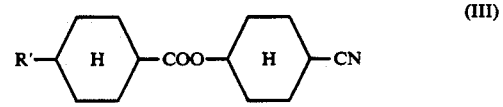

exhibit no mesophases, while the analogous phenylcyclohexyl derivatives of the formula IV

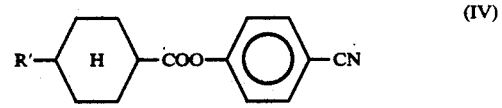

still have clear points between 70° and 80° C.

In the investigations leading to the present invention, it was found that the conformation energy of the groupings which form the anisotropic molecule, in particular the polarizing substituents, and the difference between the free conformation energy $-\Delta G_{\chi}^{\circ}$ of the groupings and substituents is of importance for their effect in reducing the clear point, and that it should be possible favorably to influence this effect by suitable choice of the substituents for longitudinal polarization and/or cross-polarization.

SUMMARY OF THE INVENTION

Thus, it is an object of this invention to provide new anisotropic compounds for LC mixtures for the operation of electrooptical displays, which enable the longitudinal polarization and/or cross-polarization problems mentioned to be solved or significantly ameliorated.

Upon further study of the application and appended claims, further objects and advantages of this invention will become apparent to those skilled in the art.

These objects have been achieved by introducing highly polarizing substituents chosen from the group comprising cyano and halogen, such as fluorine or chlorine, into the alkyl part of an end group of particular anisotropic molecules.

The invention relates to new anisotropic compounds of the formula (l)

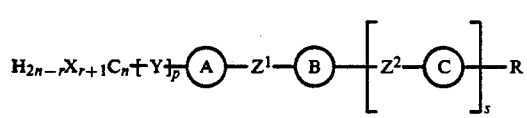

(1)

which is defined as follows: the rings A, B and C are identical or different and are chosen from the cycloaliphatic radicals of the formulae (1a) and (1b)

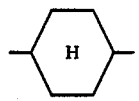

(1a)

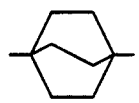

(1b)

that is to say the trans-1,4-cyclohexyl and 1,4-bicyclo(2,2,2)-octyl radicals, and aromatic radicals of the formulae (1c), (1d) and (1e)

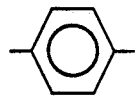

(1c)

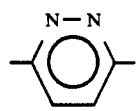

(1d)

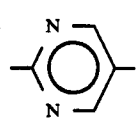

(1e)

that is to say the 1,4-phenyl, 3,6-pyridazinyl and 2,5-pyrimidinyl radicals. The radical X, that is to say the highly polarizing group, at least one or more of which are present in the molecule, is the cyano group or a halogen atom, halogen atoms being fluorine and chlorine, in preference to bromine, and iodine being least preferred. At most one X may be attached to in each case one $C_n$ atom.

Y is an optional structural component (that is to say p is 0 or 1), and is the oxygen atom (—O—), the carboxyl group (—C(O)—O— or —O(O)C—) or the imino group (—N(H)—). If A is an aliphatic ring of the formula (1a) or (1b), p is preferably 0.

The bridges $Z^1$ and $Z^2$ can be identical or different and are covalent bonds or groups of the formula —COO—, —CH$_2$O— or

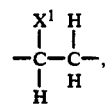

wherein $X^1$ is hydrogen or has one of the meanings given for X, and the groups can also be in the particular reverse sequence —OOC—, —OCH$_2$— and —CH$_2$C($X^1$)(H)—, as long as these are not excluded by the provisos given below.

If $X^1$ has one of the meanings given for X, that is to say is cyano or halogen (F and Cl preferred as halogen), the corresponding bridge member contributes towards cross-polarization of the molecule of the formula (1). However, $X^1$ can only be one of the X groups if the end group R or $R^1$ is also one of the X groups.

The index n is a number from 1 to 12; in a preferred group of compounds of the formula (1), r is 0 or 1, but can also be greater with a corresponding chain length of the alkyl part; r is preferably 0.

The ring C is an optional component of compounds according to the invention, that is to say s like p is 0 or 1.

R can have one of the meanings given for $X^1$ if the adjacent ring C (if s=1) or B (if s=0) is an aromatic radical of the formula (1c), (1d) or (1e); in addition, R can be an alkyl ($H_{2m+1}C_m$—), alkoxy ($H_{2m+1}C_m$—O—), alkoxycarbonyl ($H_{2m+1}C_m$—OC(O)—), alkylcarbonyloxy ($H_{2m+1}C_m$—C(O)—O—) or alkylamino ($H_{2m+1}C$—N(H)—) group, the alkyl part of which contains 1 to 12 C atoms (m=1-12) in a straight or branched, optionally chiral chain. Examples of the alkyl parts of the groups mentioned are methyl, ethyl, propyl, butyl, pentyl, hexyl, heptyl, octyl, nonyl, decyl, undecyl and dodecyl groups, including the isomeric and chiral-isomeric alkyl groups, such as 1-methylpropyl, 1-methylbutyl, 2-methylbutyl, 1-methyl-pentyl, 2-methylpentyl, 3-methylpentyl, 1- or 2- or 3- or 4-methylhexyl and 1- or 2- or 3- or 4-or 5-methylheptyl, as well as the other alkyl-alkyl groups with an asymmetric C atom which are formed according to this principle.

The alkyl parts of R can carry one or more substituents, in particular halogen atoms or cyano groups, but at most in each case one such substituent is attached to in each case one C atom of the alkyl part. Furthermore, R can be a radical of the formula (1f)

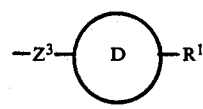

(1f)

in which the ring D independently is one of the rings given for A, B and C, $Z^3$ independently has one of the meanings given for $Z^1$ and $Z^2$ and $R^1$ has one of the meanings given for R, with the exception of the radical of the formula (1f).

According to the invention, the formula (1) is subject to the following restrictive provisos (a), (b), (c) and (d):
(a) no oxygen atom, on the one hand, and no oxygen or nitrogen atom or radical X, on the other hand, are at the same time bonded directly to any of the cycloaliphatic radicals of the formulae (1a) and (1b) present in the molecule of the formula (1); in other words, the molecule may not contain any rings of the formulae

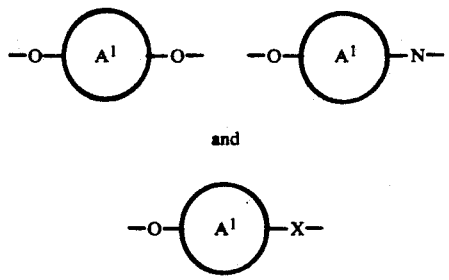

and wherein $A^1$ is a radical of the formula (1a) or (1b);
(b) no groups of the formulae —CH$_2$O— and —C(X)(H)— are bonded directly, with the C atoms of this group, to any of the aromatic radicals of the formulae (1c), (1d) and (1e) present in the molecule of the formula (1), except when X is the fluorine atom; in other words, the molecule may not contain any rings of the formulae

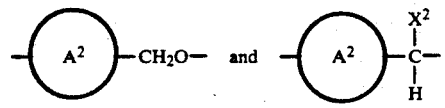

wherein $A^2$ is a radical of the formula (1c), (1d) or (1e) and $X^2$ is cyano, chlorine, bromine or iodine, but not fluorine;
(c) the molecule of the formula (1) contains a total of at least two radicals X if p, r and s are 0 and also $Z^1$ is the carboxyl group and the ring A is the radical of the formula (1c), bonded to a group of the formula —CH$_2$CH$_2$CN; the second radical X here can optionally be part of the left or right end group or can be attached to a bridge member, and
(d) $X^1$ can only be one of the meanings of X, that is to say can be cyano or halogen, if R and/or $R^1$ also have one of the meanings for X.

The provisos (a) and (b) result from the fact that compounds of the formula (1) without these provisos do not have clear points or have clear points which are too low and/or do not have the required stability. The provisos (c) and (d) serve for the purpose of delimitation.

DETAILED DESCRIPTION

The knowledge, on which the invention is based, that the introduction of polarizing substituents into end alkyl groups offers a large number of new anisotropic compounds with low $$\frac{\Delta \epsilon}{\epsilon \perp}$$

values, irrespective of whether the rings of the molecule are only cycloaliphatic radicals or only aromatic radicals, or whether cycloaliphatic radicals are combined with aromatic radicals, is new and surprising. In this case, the molecule of the new compounds (1) according to the invention contains a combination of longitudinally polarizing X and cross-polarizing X, for example a terminal X at the end of an end group or directly on an aromatic ring, together with at least one lateral X as part of an end group.

The knowledge on which the invention is based furthermore offers a large number of new, highly longitudinally polarizing anisotropic compounds, in which the longitudinally polarizing cyano or halogen atom is terminal on an alkyl radical of an end group attached to a cycloaliphatic radical; longitudinally polarizing compounds with high clear points are thereby obtainable.

This longitudinal polarization by cyano or halogen in the end group of a cycloaliphatic radical can optionally be combined with cross-polarizing cyano or halogen in an end group or/and a bridge member.

If the compound (1) according to the invention is to have a markedly positive DCA, it will in most cases carry an end group which contains or consists of a terminal X-preferably cyano. It should be taken into consideration here, as also in the overall polarization variations described below, that a non-terminal X in the end groups can also contribute towards longitudinal polarization.

If the compound (1) is to have as small as possible a value of $$\frac{\Delta \epsilon}{\epsilon \perp}$$

with a more or less markedly positive DCA, it carries an end group which contains a terminal X, preferably cyano, or consists of such a group, combined with at least one non-terminal X in an end group and/or an X on a bridge.

Compounds (1) with negative DCA are obtained when the sum of the lateral polarization contributions of X in the end groups and/or bridges exceeds the sum of the longitudinally polarizing contributions, or if the longitudinally polarizing groups are absent.

Preferred groups of compounds of the formula (1) according to the invention are those wherein the ring A is a cycloaliphatic radical of the formula (1a) or (1b); p, r and s are 0; r is 0 or 1 and R and/or $R^1$ contains an alkyl portion which is at most disubstituted; R only denotes cyano, fluorine or chlorine if the ring bonded directly to R is an aromatic radical of the formula (1c), (1d) or (1e); there is at most one carboxyl group; at least one of the bridge members $Z^1$, $Z^2$ or $Z^3$ is a covalent bond; the structure is of formula (8)

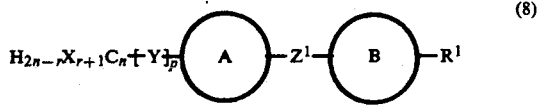

(8)

in which X, Y, A, B, $Z^1$, $R^1$, n, r and p are as defined above; the rings A and B are radicals of the formulae (1a), (1b) or/and (1c); the structure of formula (9)

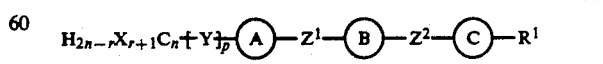

(9)

in which X, Y, A, B, C, $Z^1$, $Z^2$, $R^1$, n, p and r are as defined above; the rings A, B and C denote radicals of the formulae (1a), (1b) or/and (1c); none of the C atoms of the end group of the formula $H_{2n-r}X_{r+1}C_n[Y]_p$, which carries a radical X, is separated from the ring A by more than two atoms of the end group chain; and R or $R^1$ contains a substituted alkyl portion, wherein non of the substituents is attached to a C atom of the alkyl portion which is separated from the ring C or D by more than two chain atoms of the end group chain.

In particular, the following features, individually or in combination, are present:

the molecule contains two or not more than three cyclic radicals and a total of 1 to not more than 4 cyano or halogen radicals;

the ring A is preferably a cycloaliphatic radical, in particular one of the formula (1a);

the ring A preferably carries an $XC_{1-7}$-alkyl group, in particular a cyano-$C_{1-7}$-alkyl group;

if X is halogen, fluorine and chlorine are preferred;

if R and/or $R^1$ contain a substituted alkyl portion, this preferably carries one or two substituents, preferred halogen atoms being fluorine and chlorine;

the molecule of the formula (1) preferably contains a total of at most one carboxyl group —COO— or —OOC—;

the molecule of the formula (1) preferably contains at most one aromatic ring of the formula (1c), (1d) or (1e);

the molecule of the formula (1) contains at least one bridge member Z in the form of a covalent bond;

the molecule of the formula (2) contains two or three cycloaliphatic radicals of the formulae (1a) and/or (1b);

if R and/or $R^1$ has an alkyl portion, this preferably contains 3 to 9 C atoms;

if R and/or $R^1$ is hydrogen or one of the X groups, the adjacent ring is an aromatic radical of the formula (1c), (1d), or (1e);

the radical X in the left end group and the substituent optionally present on the alkyl portion of R and/or $R^1$ are preferably attached to a C atom of the alkyl chain which is separated from the associated ring by not more than 2 C atoms.

The following formulae illustrate the structure of specific groups of compounds according to the invention, $A^1$, $B^1$ and $C^1$ in each case independently being the cycloaliphatic radicals (1a) or (1b), $A^2$, $B^2$ and $C^2$ in each case independently being the aromatic radicals (1c), (1d) or (1e), $R^4$ being $C_{1-12}$-alkyl, $C_{1-12}$-alkoxy, $XC_{1-7}$-alkyl, cyano, F or Cl and $R^5$ being $C_{1-12}$-alkyl, $C_{1-12}$alkoxy, $C_{1-12}$alkoxycarbonyl or $C_{1-12}$-alkylcarbonyloxy; and the symbols A, B, C, $Z^1$, $Z^2$, X and $R^1$ have the abovementioned meaning. Preferably $R^4$ and $R^5$ are $C_{1-12}$-alkyl. In formula 18, the $B^2$ groups are identical.

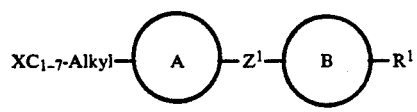
(10)

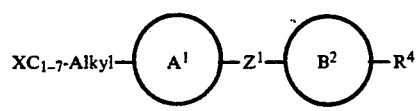
(11)

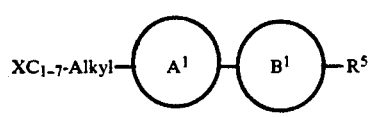
(12)

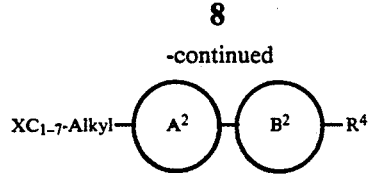
(13)

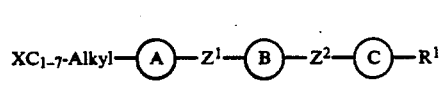
(14)

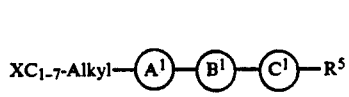
(15)

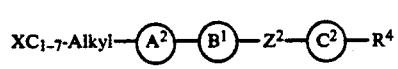
(16)

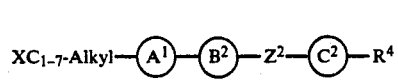
(17)

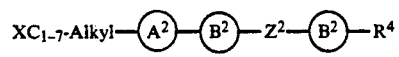
(18)

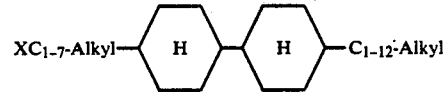
(19)

(20)

$XC_{1-7}$-Alkyl is a n-alkyl group having 1–7 C-atoms substituted by X. Preferably the substitution is at the end in ω-position. A preferred meaning of $XC_{1-7}$-Alkyl in particular is NC—$CH_2CH_2$—.

The invention also relates to liquid crystal mixtures which contain at least one compound of the formula (1), for example in amounts of 1–30 mol %, it being possible for the mixture also to contain several different compounds of the formula (1), for example in an amount of up to 90 mol % in total. As further components, the LC mixtures according to the invention can contain known anisotropic compounds and the additives corresponding to the intended use, such as dyestuffs, in particular pleochroic dyestuffs, optically active or cholesteric components and the like. The preparation, compositions and use of the liquid crystal mixtures of this invention are fully routine and conventional. See, e.g., U.S. Pat. Nos. 3,995,941; 3,951,846 and 4,285,829. In view of the chiral properties of the compounds of this invention discussed above, they are advantageously useful as a chiral component (especially when in the smectic C phase) of ferroelectric liquid crystalline phases.

The new compounds of the formula (1) can be obtained by various methods which are known per se; a first general method is based, for example, on modifying a precursor corresponding to the molecule (1), without an X radical or without X-alkyl, by introduction of X or X-alkyl, for example by halogenation, such as bromination, if appropriate transhalogenation and if appropriate nitrilation, or by Friedel-Crafts reaction and reduction in a manner which is known per se.

A second general method is based, for example, on forming the molecule (1) by combining corresponding molecular fragments, for example by condensation, esterification or etherification on a bridge member.

Corresponding precursors or molecular fragments are either known as such or can be obtained analogously to the known compounds from known or conventionally preparable starting materials.

A general example for the first method is illustrated in equation V which follows; the chain length of the X-carrying end group can be further increased by repeating the steps; bromination/carboxylation/reduction/-bromination, the radical X in each case being terminal; the formation of an alkyl-end group with a non-terminal X, for example cyano, is illustrated in equation Va, in which case a "compound (1)", that is to say a compound of the formula (1), or a corresponding "precursor" can in each case be used as the starting substance.

Equation Vb illustrates a specific example for the preparation of suitable "precursors-COOH", that is to say of corresponding carboxylic acids for the synthesis according to equation V or for the preparation of compounds of the formula (1) with terminal cyano on a ring by modification of the carboxyl group by known methods, for example directly or via the corresponding amide. "X-alkyl" in equation Vb here is a group of the formula $H_{2n'-r}X_{r+1}C_{n'}—$, in which n' is in each case one smaller than the n desired in formula (1).

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, etc., or other reactions disclosed herein or otherwise conventional, will be applicable to the preparation of the corresponding compounds of this invention.

EQUATION V

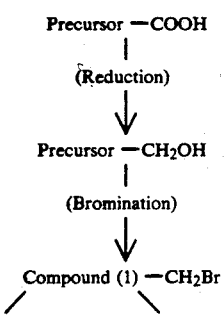

EQUATION Va

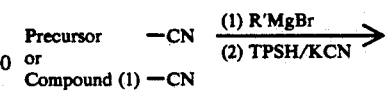

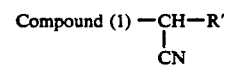

EQUATION Vb

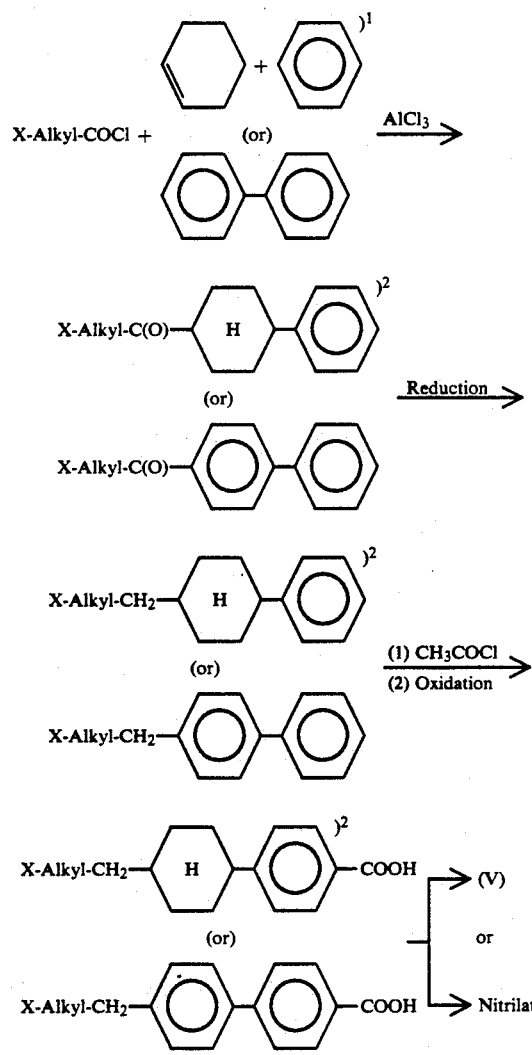

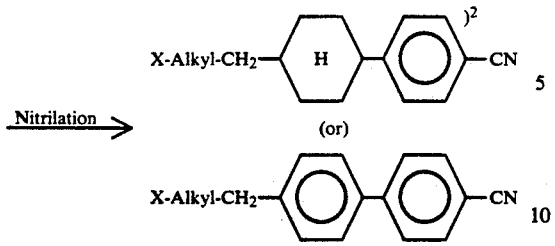

)[1] See J.A.C.S. 67 (1945) 1045
)[2] If appropriate, subsequent separation and isolation of the trans-isomers The reduction of the carboxyl compounds can be carried out with, for example, lithium aluminum hydride; the bromination is in most cases advantageously carried out with elemental bromine in the presence of triphenylphosphine, and the nitrilation is carried out, for example, with copper(I)-cyanide or KCN; the Grignard method or, in certain circumstances, nitrile group hydrolysis, is suitable for the carboxylation.

The following are general examples of known carboxyl-precursors or carboxyl-precursors which are obtainable in a known manner, $R^1$, B, C, $Z^1$ and $Z^2$ having the abovementioned meaning:

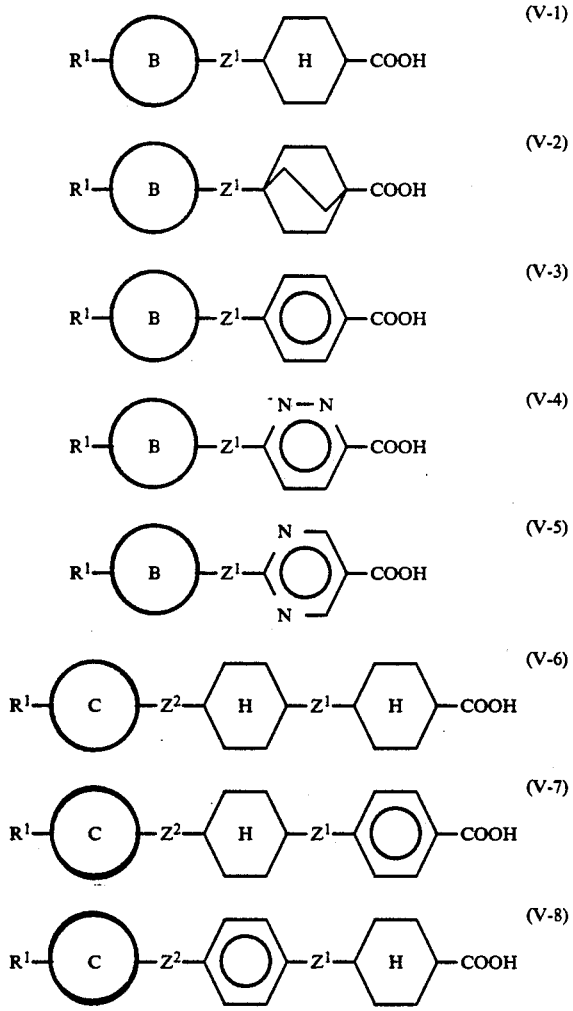

A general example of the second method for the preparation of compounds (1) according to the invention is illustrated in Equation VI below, in which the compound (1) to be prepared consists of two fragments, for example fragment$^a$ and fragment$^b$, which are bonded to one another by a bridge member Z, for example a carboxyl or methoxy group. Depending on the nature of the bridge group, the reaction is, for example, esterification, etherification or the like, and the fragment can carry a part ($Z^a$, $Z^b$) of the bridge to be formed; $L^1$ and $L^2$ are corresponding leaving groups.

EQUATION VI

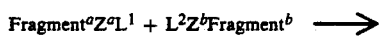

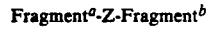

Suitable compounds for the synthesis according to Equation VI are also either known or can be obtained in a manner which is known per se. Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Preparation of 4-trans-cyanoethyl-cyclohexyl 4-trans-propyl-cyclohexyl-1-carboxylate 4-trans-propyl-cyclohexane-1-carboxylic acid (25 mmol) was warmed with thionyl chloride (40 ml) at the reflux temperature for 30 minutes. The acid chloride formed was freed from excess thionyl chloride. The acid chloride thus obtained was now added dropwise to a solution of 4-trans-cyanoethyl-cyclohexanol (melting point 52° C., 25 mmol, obtainable as follows: 2-(4-hydroxyphenyl)-propionamide was catalytically hydroginated in 95% acetic acid (Nishimura catalyst). The resulting 1:1 cis-trans-mixture was equilibrated with aluminium isopropylate. The resulting trans alcohol was acetylated, converted to the nitrile by SOCl$_2$ and finally the acetyl group was hydrolized with NaOH) in 100 ml of pyridine. When the reaction had ended, the mixture was poured into excess dilute hydrochloric acid and extracted with methylene chloride. The product obtained from the extract by evaporation was recrystallized. The target compound of this example thus obtained is monotropically liquid crystal and has a melting point of 73.0° C. and a clear point of 14.6° C.

EXAMPLE 2

Preparation of 4-trans-cyanoethyl-cyclohexyl 4-trans-pentyl-cyclohexyl-1-carboxylate 4-trans-pentyl-cyclohexane-1-carboxylic acid (36.5 mmol) was boiled under reflux with thionyl chloride (50 ml) for 1 hour. The excess thionyl chloride was distilled. The resulting acid chloride was added dropwise to a solution of 36.5 mmol of 4-trans-cyanoethyl-cyclohexyl in 100 ml of pyridine. The reaction mixture was stirred until the reaction had ended and then poured onto dilute hydrochloric acid. The product was extracted with methylene chloride. For purification, the product was recrystallized. It has a monotropic liquid crystal phase and a melting point of 61.5° C. and a clear point of 39.3° C.

EXAMPLES 3-7

By the process described in Equation V or Va and from the corresponding carboxylic acids of the formula (30)

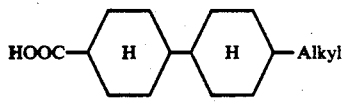

the compounds of the formula (31) according to the invention

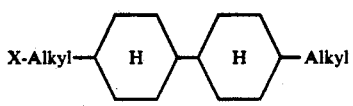

are prepared and their transition temperatures are determined.

The results are summarized in the following Table I

TABLE I

| Example | X-alkyl | alkyl | melting point | clear point (°C.) | |
|---|---|---|---|---|---|
| 3 | Br—CH$_2$—CH$_2$— | n-pentyl | 46.0 | 67.9 | |
| 4 | NC—CH$_2$—CH$_2$— | n-pentyl | 9 | 108.8 | |
| 5 | NC—CH$_2$— | n-pentyl | 56.5 | 82.6 | ε∥ 9.0 ε⊥ 8.5 |
| 6 | Br—CH$_2$— | n-propyl | 44.4 | (36.1) | |
| 7 | H$_3$C(CH$_2$)$_3$C(H)(CN)— | n-pentyl | 35 | 80.0 | |

EXAMPLE 7a

Preparation of 4-trans-cyanoethyl-4'-trans-propyl bicyclohexane according to Equation V:

Step 1: A solution of 4'-propyl-trans, trans-bicyclohexane-4-carboxylic acid (0.1M) [R. Eidenschink, D. Erdmann, J. Krause and L. Pohl, Angew. Che. Int. Ed. 17, 133 (1978)] in dry THF was added dropwise to a suspension of LiAlH$_4$ (10 g) in 100 ml of dry THF at 0° C. The reaction mixture was then refluxed for 1 h, poured over cold dilute HCl and the product was extracted in ether.

Step 2: Bromine (0.12M) was added dropwise to a suspension of P(Ph)$_3$ (0.12M) in dry CH$_3$CN at 0° C. and the mixture stirred for 30 min at room temperature. To this suspension, a solution of the alcohol prepared above in dry CH$_3$CN was added dropwise and the mixture stirred for 15 min at this temperature. The solvent was then distilled off and the reactants heated for 30 min at 130° C. After usual working up the reaction mixture, the raw product was extracted in CH$_2$Cl$_2$ and the solution was added to hexane to precipitate the triphenylphosphine oxide. The product was purified by chromatography (silica gel/toluene).

Step 3: A solution of the above prepared bromide in dry ether was added dropwise to a suspension of magnesium (4 g) in dry ether and the mixture stirred at room temperature for 1 h. Dry CO$_2$ gas was then passed through the reaction mixture for 30 min, before it was worked up in the usual way. The raw product was crystallized from toluene or hexane. Steps 1 and 2 were then repeated using this product as a starting material.

Step 4: A mixture of the so prepared 4-trans-bromoethyl-4'-trans-propyl bicyclohexane and solid KCN was heated at 100° C. for 2 h in DMSO and then poured onto water. The reaction product was extracted in ether and filtered through a short silica gel column using toluene as a solvent. It was crystallized from EtOH, melting point 13° C., clear point 99° C.

EXAMPLES 8-12

By the process according to Equation V or Va and from the corresponding carboxylic acids of the formula (80)

the corresponding compounds of the formula (81) according to the invention

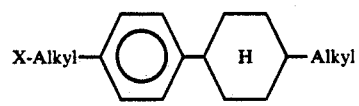

are prepared. The resulting anisotropic compounds are summarised in the following Table II.

TABLE II

| Example | X-alkyl | alkyl | melting point | clear point (°C.) |
|---|---|---|---|---|
| 8 | Br—CH$_2$—CH$_2$— | n-pentyl | 30 | |
| 9 | I—CH$_2$—CH$_2$— | n-pentyl | 36.2 | |
| 10 | NC—CH$_2$—CH$_2$— | n-pentyl | 44.8 | (28.3) |
| 11 | Br—CH$_2$— | n-pentyl | 28.6 | |
| 12 | H$_3$C(CH$_2$)$_3$C(H)(CN)— | n-pentyl | 34. | |

EXAMPLE 13

Preparation of 4-cyanoethylphenyl-4-trans-pentyl-cyclohexyl-1-carboxylate

A solution of trans-4-pentylcyclohexane carboxylic acid chloride (0.1M) in pyridine, was added dropwise to a stirred solution of 4-trans-cyanoethyl-cyclohexanol (0.1M) in pyridine at 0°-5° C., and the mixture stirred at this temperature for 2 h. The reaction mixture was then worked up in the usual way and the product crystallized twice from methanol, melting point 75° C., clear point 51° C.

Other examples of compounds of the formula (1) are the following. They can be prepared as described above.

4-fluoromethyl-4'-pentyl-biphenyl
4-fluoromethyl-4'-cyano-biphenyl
4-(2-fluoroethyl)-4'-cyano-biphenyl
4-(2-chloroethyl)-4'-bromo-biphenyl
4-(2-chloroethyl)-4'-(2-cyanoethyl)-biphenyl
4,4'-bis-(2-chloroethyl)-biphenyl
4,4'-bis-(2-fluoroethyl)-biphenyl
4-(3-fluoropropyl)-4'-cyano-biphenyl
4-(3-chloropropyl)-4'-butoxy-biphenyl
4-(3-(fluoropropyl)-4'-bromo-biphenyl
4-(3-cyanopropyl)-4-pentyl-biphenyl 4-(3-cyanopropyl)-4-fluoromethyl-biphenyl
4-(3-chloropropyl)-4-(2-fluoroethyl)-biphenyl
4-(3-fluoropropyl)-4-(3-bromopropyl)-biphenyl
4-(3-cyanopropyl)-4-(3-fluoropropyl)-biphenyl
4,4'-bis-(3-cyanopropyl)-biphenyl
4,4'-bis-(3-chloropropyl)-biphenyl
4,4'-bis-(3-bromopropyl)-biphenyl
4,4'-bis-(3-fluoropropyl)-biphenyl
4-(4-cyanobutyl-4'-cyano-biphenyl
4-(4-chlorobutyl)-4'-bromo-biphenyl
4-(4-fluorobutyl)-4'-butoxy-biphenyl
4-(4-bromobutyl)-4'-fluoro-biphenyl
4,4'-bis-(4-cyanobutyl)-biphenyl
4,4'-bis-(4-chlorobutyl)-biphenyl
4,4'-bis-(4-fluorobutyl)-biphenyl
4,4'-bis-(4-bromobutyl)-biphenyl
4-(4-cyanobutyl)-4'-(2-cyanoethyl)-biphenyl
4-(4-cyanobutyl)-4'-(4-fluorobutyl)-biphenyl
4-(4-chlorobutyl)-4'-(3-fluoropropyl)-biphenyl
4-(4-fluorobutyl)-4'-cyano-biphenyl
4-(2-fluorobutyl)-4'-cyano-biphenyl
4-(1-fluoropentyl)-4'-cyano-biphenyl
4-(2-fluoropentyl)-4'-cyano-biphenyl
4-(3-fluoropentyl)-4'-cyano-biphenyl
4-(5-fluoropentyl)-4'-cyano-biphenyl
4-fluoromethyl-4''-butoxy-p-terphenyl
4-fluoromethyl-4'''-fluoro-p-terphenyl
4-fluoromethyl-4'''-cyano-p-terphenyl
4-cyanomethyl-4'''-pentyl-p-terphenyl
4,4''-bis-(fluoromethyl)-p-terphenyl
4-(2-fluoroethyl)-4'''-cyano-p-terphenyl
4-(2-chloroethyl)-4'''-butoxy-p-terphenyl
4-(2-fluoroethyl)-4'''-chloro-p-terphenyl
4-(2-cyanoethyl)-4'''-chloro-p-terphenyl
4-(2-cyanoethyl)-4'''-(3-fluoropropyl)-p-terphenyl
4-(2-chloroethyl)-4''-(2-fluoropropyl)-p-terphenyl
4-(2-bromoethyl)-4'''-cyanomethyl-p-terphenyl
4-(2-fluoroethyl)-4'''-bromomethyl-p-terphenyl
4,4''-bis-(2-chloroethyl)-p-terphenyl
4,4''-bis-(2-fluoroethyl)-p-terphenyl
4,4''-bis-(2-bromoethyl)-p-terphenyl
4,4''-bis-(2-cyanoethyl)-p-terphenyl
4-(1-fluoropentyl)-4''-cyano-p-terphenyl
4-(2-fluoropropyl)-4''-cyano-p-terphenyl
4-(3-fluoropropyl)-4''-cyano-p-terphenyl
4-(5-fluoropentyl)-4''-cyano-p-terphenyl
4-(3-chloropropyl)-4''-pentyl-p-terphenyl
4-(3-chloropropyl)-4''-chloromethyl-p-terphenyl
4-(3-bromopropyl)-4''-(2-fluoroethyl)-p-terphenyl
4-(3-cyanopropyl)-4'''-(3-chloropropyl)-p-terphenyl
4,4''-bis-(3-cyanopropyl)-p-terphenyl
1-(4-fluoromethylphenyl)-2-(4-cyanophenyl)-ethane
1-(4-(2-cyanoethyl)-phenyl)-2-(4-pentylphenyl)-ethane
1-(4-(3-chloropropyl)-phenyl)-2-(4-cyanomethyl-phenyl)-ethane
1-(4-(4-bromobutyl)-phenyl)-2-(4-(3-cyanopropyl)-phenyl-ethane
1-(4-(3-fluoropropyl)-phenyl)-2-(4-cyanophenyl)-ethane
1-(4-(3-fluoropropyl)-phenyl)-2-(4-(2-cyanoethyl)-phenyl)-ethane
1,2-bis-(4-fluoromethylphenyl)-ethane
1,2-bis-(4-(4-cyanobutyl)-phenyl)-ethane
4,4''-bis-(4-cyanobutyl)-p-terphenyl
4,4''-bis-(4-chlorobutyl)-p-terphenyl
4'-(4-chlorobutyl)-4''-butoxy-p-terphenyl
1-(4-trans-(1-fluoropentyl)-cyclohexyl)-4-cyano-benzene
1-(4-trans-fluoromethyl-cyclohexyl)-4-cyano-benzene
1-(4-trans-(5-fluoropentyl)-cyclohexyl)-4-cyano-benzene
1-(4-trans-(2-cyanoethyl)-cyclohexyl)-4-butoxy-benzene
1-(4-trans-(3-chloropropyl)-cyclohexyl)-4-(2-cyanoethyl)-benzene
1-(4-trans-(4-bromobutyl)-cyclohexyl)-4-(3-fluoropropyl)-benzene
1-(4-trans-(4-chlorobutyl)-cyclohexyl)-4-pentyl-benzene
1-(4-trans-(3-fluoropropyl)-cyclohexyl)-4-(3-fluoropropyl)-benzene
1-(4-trans-(2-fluoropentyl)-cyclohexyl)-4-cyano-benzene
1-(4-trans-(3-fluoropentyl)-cyclohexyl)-4-cyano-benzene
1-(4-trans-(2-cyanoethyl)-cyclohexyl)-2-(4-cyanophenyl)-ethane
1-(4-trans-(3-fluoropropyl)-cyclohexyl)-2-(4-(2-cyanoethyl)-phenyl)-ethane
1-(4-trans-(4-chlorobutyl)-cyclohexyl)-2-(4-pentylphenyl)-ethane
1-(4-trans-fluoromethyl-cyclohexyl)-2-(4-butoxyphenyl)-ethane
4-(4-trans-(2-cyanoethyl)-cyclohexyl)-4'-(3-fluoropropyl)-biphenyl
4-(4-trans-(3-fluoropropyl)-cyclohexyl)-4'-cyano-biphenyl
4-(4-trans-(5-fluoropentyl)-cyclohexyl)-4'-cyano-biphenyl
4-(4-trans-(cyanomethyl-cyclohexyl)-4'-pentyl-biphenyl
4-(4-trans-(fluoromethyl-cyclohexyl)-4'-fluoromethyl-biphenyl
1-(4-trans-(2-chloroethyl)-cyclohexyl)-2-(4'-butoxybiphenyl-4-yl)-ethane
1-(4-trans-(3-fluoropropyl)-cyclohexyl)-2-(4'-cyanobiphenyl-4-yl)-ethane
1-(4-trans-(4-cyanobutyl)-cyclohexyl)-2-(4'-(3-fluoropropyl)-biphenyl-4-yl)-ethane
1-(4-trans-(bromoethyl-cyclohexyl)-2-(4'-(2-cyanoethyl)biphenyl-4-yl)-ethane
1-(4-fluoromethyl-1-bicyclo-(2,2,2)-octyl)-4-cyano-benzene
1-(4-(2-chloroethyl)-1-bicyclo-(2,2,2)-octyl)-4-pentylbenzene
1-(4-(3-cyanopropyl)-1-bicyclo-(2,2,2)-octyl)-4-(3-fluoropropyl)-benzene
1-(4-(4-bromobutyl)-1-bicyclo-(2,2,2)-octyl)-4-butoxybenzene
4-(4-fluoromethyl-1-bicyclo-(2,2,2)-octyl)-4'-pentylbiphenyl
4-(4-(2-cyanoethyl)-1-bicyclo-(2,2,2)-octyl)-4'-(3-fluoropropyl)-biphenyl
4-(4-(3-bromopropyl)-1-bicyclo-(2,2,2)-octyl)-4'-(2-cyanoethyl)-biphenyl
4-(4-(4-chlorobutyl)-1-bicyclo-(2,2,2)-octyl)-4'-butoxybiphenyl
4-(4-(3-fluoropropyl)-1-bicyclo-(2,2,2)-oxtyl)-4'-cyanobiphenyl
3-(4-(3-fluoropropyl)-phenyl)-6-pentyl-pyridazine
3-(4-(2-cyanoethyl)-phenyl)-6-butoxy-pyridazine
3-(4-(3-chloropropyl)-phenyl)-6-butoxy-pyridazine
1-(4-fluoromethylphenyl)-2-(6-pentylpyridazin-3-yl)-ethane
1-(4-(2-cyanoethyl)-phenyl)-2-(6-butoxypyridazin-3-yl)-ethane 1-(4-(3-bromopropyl)-phenyl)-2-(6-butoxypyridazin-3-yl)-ethane
1-(4-(4-chlorobutyl)-phenyl)-2-(6-pentylpyridazin-3-yl)-ethane
3-(4-fluoromethylphenyl)-6-(4-pentylphenyl)-pyridazine
3-(4-(2-chloroethyl)-phenyl)-6-(4-butoxyphenyl)-pyridazine
3-(4-(3-fluoropropyl)-phenyl)-6-(4-pentylphenyl)-pyridazine
3-(4-(4-cyanobutyl)-phenyl)-6-(4-butoxyphenyl)-pyridazine
3-(4-(4-cyanobutyl)-phenyl)-6-(4-pentylphenyl)-pyridazine -p0 3-(4-(3-fluoropentyl)-phenyl)-6-(4-cyanophenyl)-pyridazine
3-(4-trans-(bromomethyl-cyclohexyl)-6-(4-butoxyphenyl)-pyridazine
3-(4-trans-(2-cyanoethyl)-cyclohexyl)-6-(4-pentylphenyl)-pyridazine
3-(4-trans-(3-chloropropyl)-cyclohexyl)-6-(4-butoxyphenyl)-pyridazine
3-(4-trans-(4-bromobutyl)-cyclohexyl)-6-(4-pentylphenyl)-pyridazine
3-(4-trans-(4-fluorobutyl)-cyclohexyl)-6-(4-cyanophenyl)-pyridazine
3-(2-(4-trans-cyanomethyl-cyclohexyl)-ethyl)-6-(4-pentylphenyl)-pyridazine
3-(2-(4-trans-(2-chloroethyl)-cyclohexyl)-ethyl)-6-(4-butoxyphenyl)-pyridazine
3-(2-(4-trans-(3-fluoropropyl)-cyclohexyl)-ethyl)-6-(4-pentylphenyl)-pyridazine
3-(2-(4-trans-(4-bromobutyl)-cyclohexyl)-ethyl)-6-(4-butoxyphenyl)-pyridazine
3-(2-(4-trans-(5-fluoropentyl)-cyclohexyl)-ethyl)-6-(4-cyanophenyl)-pyridazine
3-(4-trans-chloromethyl-cyclohexyl)-6-pentyl-pyridazine
3-(4-trans-(2-cyanoethyl)-cyclohexyl)-6-butoxy-pyridazine
3-(4-trans-(3-fluoropropyl)-cyclohexyl)-6-butoxy-pyridazine
3-(4-trans-(4-bromobutyl)-cyclohexyl)-6-pentyl-pyridazine
1-(4-trans-cyanomethyl-cyclohexyl)-2-(6-pentyl-3-pyridazine)-ethane
1-(4-trans-(2-bromoethyl)-cyclohexyl)-2-(6-butoxy-3-pyridazine)-ethane
1-(4-trans-(3-chloropropyl)-cyclohexyl)-2-(6-pentyl-3-pyridazine)-ethane
1-(4-trans-(4-fluorobutyl)-cyclohexyl)-2-(6-butoxy-3-pyridazine)-ethane
1-(4-trans-(3-fluoropropyl)-cyclohexyl)-2-(6-butoxy-3-pyridazine)-ethane
2-(4-cyanophenyl)-5-(3-fluoropropyl)-pyrimidine
2-(4-(2-cyanoethyl)-phenyl)-5-(2-chloroethyl)-pyrimidine
2-(4-(3-chloropropyl)-phenyl)-5-pentyl-pyrimidine
2-(4-(4-fluorobutyl)-phenyl)-5-(2-cyanoethyl)-pyrimidine
2-(4-(fluoromethylphenyl)-5-(4-cyanophenyl)-pyrimidine
2-(4-fluoromethylphenyl)-5-(4-(2-fluoroethyl)-phenyl)-pyrimidine
2-(4-(2-bromoethyl)-phenyl)-5-(4-pentylphenyl)-pyrimidine
2-(4-(3-chloropropyl)-phenyl)-5-(4-(3-fluoropropyl)-phenyl)-pyrimidine
2-(4-(4-trans-bromomethyl-cyclohexyl)-phenyl)-5-pentyl-pyrimidine
2-(4-(4-trans-(2-chloroethyl)-cyclohexyl)-phenyl)-5-(3-fluoropropyl)-pyrimidine
2-(4-(4-trans-(3-fluoropropyl)-cyclohexyl)-phenyl)-5-(2-bromoethyl)-pyrimidine
2-(4-(4-trans-(4-cyanobutyl)-cyclohexyl)-phenyl)-5-(4-cyanobutyl)-pyrimidine
2-(4-(4-trans-(4-fluorobutyl)-cyclohexyl)-phenyl)-5-pentylpyrimidine
2-(4-(4-trans-cyanomethyl-cyclohexyl)-phenyl)-5-pentyl-pyrimidine
1-(4-trans-chloromethyl-cyclohexyl)-2-(4-(5-pentyl-2-pyrimidine)-phenyl)-ethane
1-(4-trans-(2-cyanoethyl)-cyclohexyl)-2-(4-(5-(2-chloroethyl)-2-pyrimidine)-phenyl)-ethane
1-(4-trans-(3-fluoropropyl)-cyclohexyl)-2-(4-(5-(3-bromopropyl)-2-pyrimidine)-phenyl)-ethane
1-(4-trans-(4-bromobutyl)-cyclohexyl)-2-(4-(5-butoxy-2-pyrimidine)-phenyl)-ethane
1-(4-trans-(2-cyanoethyl)-cyclohexyl)-2-(4-(5-(3-fluoropropyl)-2-pyrimidine)-phenyl)-ethane
4-trans-cyanomethyl-4'-trans-propyl-bicyclohexane
4-trans-(2-bromoethyl)-4'-trans-propyl-bicyclohexane
4-trans-(3-fluoropropyl)-4'-trans-pentyl-bicyclohexane
4-trans-(2-cyanoethyl)-4'-trans-propyl-bicyclohexane
4-trans-(2-cyanoethyl)-4'-trans-pentyl-bicyclohexane
4-trans-(2-bromoethyl)-4'-trans-pentyl-bicyclohexane
4-trans-bromomethyl-4'-trans-propyl-bicyclohexane
4-trans-bromomethyl-4'-trans-pentyl-bicyclohexane
4-trans-cyanomethyl-4'-trans-pentyl-bicyclohexane
4-trans-(4-bromobutyl)-4'-trans-pentyl-bicyclohexane
4-trans-(4-cyanobutyl)-4'-trans-propyl-bicyclohexane
4-trans-chloromethyl-4'-trans-propyl-bicyclohexane
4-trans-(2-chloroethyl)-4'-trans-pentyl-bicyclohexane
1-(4-trans-cyanomethyl-cyclohexyl)-2-(4-trans-pentyl-cyclohexyl)-ethane
1-(4-trans-(2-chloroethyl)-cyclohexyl)-2-(4-trans-propylcyclohexyl)-ethane
1-(4-trans-(3-fluoropropyl)-cyclohexyl)-2-(4-trans-pentylcyclohexyl)-ethane
1-(4-trans-(4-cyanobutyl)-cyclohexyl)-2-(4-trans-pentylcyclohexyl)-ethane
1-(4-trans-(4-bromobutyl)-cyclohexyl)-2-(4-trans-propylcyclohexyl)-ethane
4-bromomethyl-4''-propyl-p-ter-trans-cyclohexane
4-(2-chloroethyl)-4''-pentyl-p-ter-trans-cyclohexane
4-(3-fluoropropyl)-4''-propyl-p-ter-trans-cyclohexane
4-(cyanobutyl)-4''-pentyl-p-ter-trans-cyclohexane
1-(4-trans-cyanomethyl-cyclohexyl)-4-propyl-bicyclo(2,2,2)-octane
1-(4-trans-(2-bromoethyl)-cyclohexyl)-4-pentyl-bicyclo-(2,2,2)-octane
1-(4-trans-(3-fluoropropyl)-cyclohexyl)-4-propyl-bicyclo-(2,2,2)-octane
1-(4-trans-(4-chlorobutyl)-cyclohexyl)-4-pentyl-bicyclo-(2,2,2)-octane
1-(4-trans-chloromethyl-cyclohexyl)-2-(4-propyl-1-bicyclo-(2,2,2)-octyl)-ethane
1-(4-trans-(2-bromoethyl)-cyclohexyl)-2-(4-pentyl-1-bicyclo-(2,2,2)-octyl)-ethane
1-(4-trans-(3-cyanopropyl)-cyclohexyl)-2-(4-propyl-1-bicyclo-(2,2,2)-octyl)-ethane
1-(4-trans-(4-fluorobutyl)-cyclohexyl)-2-(4-pentyl-1-bicyclo-(2,2,2)-octyl)-ethane
4-trans-fluoromethyl-4''-trans-(4-propyl-1-bicyclo-(2,2,2)-octyl)-bicyclohexane 4-trans-(2-cyanoethyl)-4'''-trans-(4-pentyl-1-bicyclo-(2,2,2)-octyl)-bicyclohexane
4-trans-(3-chloropropyl)-4'''-trans-(4-propyl-1-bicyclo-(2,2,2)-octyl)-bicyclohexane
4-trans-(4-bromobutyl)-4'''-trans-(4-pentyl-1-bicyclo-(2,2,2)-octyl)-bicyclohexane
4-trans-(4-fluorobutyl)-4'''-trans-(4-pentyl-1-bicyclo-(2,2,2)-octyl)-bicyclohexane
4-trans-(3-cyanopropyl)-4'''-trans-(4-pentyl-1-bicyclo-(2,2,2)-octyl)-bicyclohexane
4-trans-(2-bromoethyl)-4'''-trans-(4-propyl-1-bicyclo-(2,2,2)-octyl)-bicyclohexane
4-trans-fluoromethyl-cyclohexyl 4-butoxy-benzoate
4-trans-(2-cyanoethyl)-cyclohexyl 4-cyano-benzoate
4-trans-(2-cyanoethyl)-cyclohexyl 4-pentyl-benzoate
4-trans-(3-fluoropropyl)-cyclohexyl 4-(2-cyanoethyl)-benzoate
4-trans-(4-bromobutyl)-cyclohexyl 4-chloro-benzoate
1-(4-trans-chloromethyl-cyclohexyl)-methoxy-4-pentylbenzene
1-(4-trans-(2-cyanoethyl)-cyclohexyl)-methoxy-4-butoxybenzene
1-(4-trans-(3-bromopropyl)-cyclohexyl)-methoxy-4-cyanobenzene
1-(4-trans-(4-fluorobutyl)-cyclohexyl)-methoxy-4-fluorobenzene
4-trans-bromomethyl-cyclohexyl 4-trans-(4-pentylphenyl)-cyclohexane-1-carboxylate
4-trans-(2-cyanoethyl)-cyclohexyl 4-trans-(4-butoxyphenyl)-cyclohexane-1-carboxylate
4-trans-(3-chloropropyl)-cyclohexyl 4-trans-(4-cyanophenyl)-cyclohexane-1-carboxylate
4-trans-(4-fluorobutyl)-cyclohexyl 4-trans-(4-chlorophenyl)-cyclohexane-1-carboxylate
1-(4-trans-(4-pentylphenyl)-cyclohexyl)-methoxy-4-trans-cyanomethyl-cyclohexane
1-(4-trans-(4-butoxyphenyl)-cyclohexyl)-methoxy-4-trans-(2-bromoethyl)-cyclohexane
1-(4-trans-(4-cyanophenyl)-cyclohexyl)-methoxy-4-trans-(3-fluoropropyl)-cyclohexane
1-(4-trans-(4-fluorophenyl)-cyclohexyl)-methoxy-4-trans-(4-chlorobutyl)-cyclohexane
4-trans-chloromethyl-cyclohexyl 4-(4-trans-pentylcyclohexyl)-benzoate
4-trans-(2-cyanoethyl)-cyclohexyl 4-(4-trans-(2-cyanoethyl)-cyclohexyl)-benzoate
4-trans-(3-bromopropyl)-cyclohexyl 4-(4-trans-(3-fluoropropyl)-cyclohexyl)-benzoate
4-trans-(4-fluorobutyl)-cyclohexyl 4-(4-trans-(4-chlorobutyl)-cyclohexyl)-benzoate
4-trans-(2-cyanoethyl)-cyclohexyl 4-(4-trans-pentyl-cyclohexyl)-benzoate
1-(4-trans-bromomethyl-cyclohexyl)-4-(4-trans-cyanomethyl-cyclohexyl)-methoxy-benzene
1-(4-trans-pentyl-cyclohexyl)-4-(4-trans-(2-bromoethyl)-cyclohexyl)-methoxy-benzene
1-(4-trans-(2-cyanoethyl)-cyclohexyl)-4-(4-trans-(3-fluoropropyl)-cyclohexyl)-methoxy-benzene
1-(4-trans-(3-chloropropyl)-cyclohexyl)-4-(4-trans-(4-bromobutyl)-cyclohexyl)-methoxy-benzene
4-trans-(fluoromethyl)-cyclohexyl-4'-(2-cyanoethyl)-bicyclohexane-4-carboxylate
4-trans-(2-cyanoethyl)-cyclohexyl-4'-(3-fluoropropyl)-bicyclohexane-4-carboxylate
4-trans-(3-chloropropyl)-cyclohexyl-4'-(pentyl)-bicyclohexane-4-carboxylate
4-trans-(4-bromobutyl)-cyclohexyl-4'-(2-chloroethyl)-bicyclohexane-4-carboxylate
1-(4'-pentylbicyclohex-4-yl)-methoxy-4-trans-fluoromethyl-cyclohexane
1-(4'-(2-cyanoethyl)-bicyclohex-4-yl)-methoxy-4-trans-(2-cyanoethyl)-cyclohexane
1-(4'-(3-fluoropropyl)-bicyclohex-4-yl)-methoxy-4-trans-(3-fluoropropyl)-cyclohexane
1-(4'-(4-chlorobutyl)-bicyclohex-4-yl)-methoxy-4-trans-(4-bromobutyl)-cyclohexane
4-trans-bromomethyl-cyclohexyl 4-pentyl-bicyclo-(2,2,2)-octane-1-carboxylate
4-trans-(2-cyanoethyl)-cyclohexyl-4-(2-cyanoethyl)-bicyclo-(2,2,2)-octane-1-carboxylate
4-trans-(3-chloropropyl)-cyclohexyl-4-(3-fluoropropyl)-bicyclo-(2,2,2)-octane-1-carboxylate
4-trans-(4-fluorobutyl)-cyclohexyl-4-(4-cyanobutyl)-bicyclo-(2,2,2)-octane-1-carboxylate
1-(4-pentyl-1-bicyclo-(2,2,2)-octyl)-methoxy-4-trans-cyanomethyl-cyclohexane
1-(4-(2-cyanoethyl)-1-bicyclo-(2,2,2)-octyl)-methoxy-4-trans-(2-cyanoethyl)-cyclohexane
1-(4-(3-fluoropropyl)-1-bicyclo-(2,2,2)-octyl)-methoxy-4-trans-(3-chloropropyl)-cyclohexane
1-(4-(4-chlorobutyl)-bicyclo-(2,2,2)-octyl)-methoxy-4-trans-(4-fluorobutyl)-cyclohexane Examples of liquid crystal mixtures according to the invention:

EXAMPLE A

A liquid crystal mixture is prepared from
9% 2-p-cyanophenyl-5-propyl-1,3-dioxane
12% 2-p-cyanophenyl-5-butyl-1,3-dioxane
9% 2-p-cyanophenyl-5-pentyl-1,3-dioxane
6% 2-p-octoxyphenyl-5-pentyl-pyrimidine
5% 2-p-nonoxyphenyl-5-pentyl-pyrimidine
5% 2-p-heptoxyphenyl-5-hexyl-pyrimidine
4% 2-p-nonoxyphenyl-5-hexyl-pyrimidine
6% 4,4'-bis-(trans-4-propylcyclohexyl)-biphenyl
9% 4-(trans-4-pentylcyclohexyl)-4'-(trans-4-propylcyclohexyl)-biphenyl
17% r-1-cyano-1-pentyl-cis-4-(trans-4-propylcyclohexyl)-cyclohexane and
18% 4-trans-cyanoethyl-4'-trans-propylbicyclohexane.

EXAMPLE B

A liquid crystal mixture is prepared from
27% trans,trans-4-pentylcyclohexylcyclohexane-4'-carbonitrile
17% trans,trans-4-propylcyclohexylcyclohexane-4'-carbonitrile
30% 4-trans-cyanoethyl-4'-trans-pentyl-bicyclohexane
16% trans-4-propylcyclohexanecarboxylic acid (p-ethoxyphenylester) and
10% trans,trans-4-pentyl-4'-butyryloxybicyclohexane.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed:

1. In a nematic liquid crystalline mixture comprising at least two liquid crystalline components, the improvement wherein at least one of said components is an anisotropic compound of formula (1)

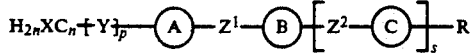

(1)

wherein the rings A, B and C are identical or different and each is a cycloaliphatic radical of the formula (1a) or (1b)

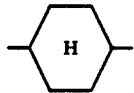

(1a)

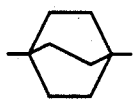

(1b)

or an aromatic radical of the formula (1c), (1d) or (1e)

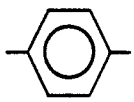

(1c)

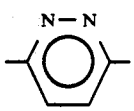

(1d)

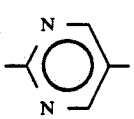

(1e)

X is halogen in omega position;

Y is —O—, —C(O)O—, —O(O)C—, or —NH—;

$Z^1$ and $Z^2$ are identical or different and each is a covalent bond, —COO—, —OOC—, —CH$_2$O—, —OCH$_2$—, or —CH$_2$—CH$_2$—;

n is an integer from 2 to 12;

p and s are identical or different and each is 0 or 1; and

R is alkyl, alkoxy, alkoxycarbonyl, alkylcarbonyloxy or alkylamino, the alkyl part of which in each case contains 1 to 12 C atoms, with the provisos that (a) when an oxygen atom is bonded directly to one of the cycloaliphatic radicals of the formula (1a) or (1b) present in the molecule, then no other oxygen atom and no nitrogen atom or radical X is bonded directly to that cycloaliphatic radical of the formula (1a) or (1b) present in the molecule, at the same time; and (b) no groups of the formulae —CH$_2$O— are bonded directly to any of the aromatic radicals of the formulae (1c), (1d) or (1e) present in the molecule.

2. A mixture of claim 1, wherein, in formula (1), the ring A in formula (1) is a cycloaliphatic radical of the formula (1a) or (1b).

3. A mixture of claim 1, wherein, in formula (1), p and s are 0.

4. A mixture of claim 1, wherein, in formula (1), the ring A in formula (1) is an aromatic radical of the formula (1c), (1d) or (1e).

5. A mixture of claim 1, wherein, in formula (1), the compound of the formula (1) contains at most one —COO— or —OOC— group.

6. A mixture of claim 1, wherein, in formula (1), at least one of the bridge members $Z^1$ or $Z^2$ is a covalent bond.

7. A mixture of claim 1, wherein at least one liquid crystalline component is of the formula (8)

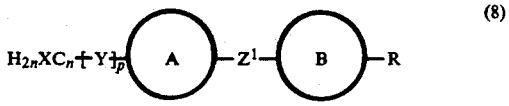

(8)

in which X, Y, A, B, $Z^1$, R, n and p are as defined in claim 1.

8. A mixture of claim 7, wherein, in formula (8), the rings A and B are radicals of the formula (1a), (1b), or (1c).

9. A mixture of claim 7, wherein, in formula (8), the rings A and B are radicals of the formula (1c), (1d) or (1e).

10. A mixture of claim 1, wherein at least one liquid crystalline component is of the formula (9)

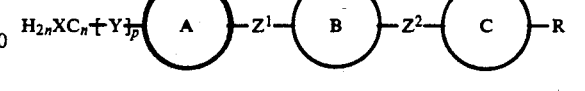

(9)

in which X, Y, A, B, C, $Z^1$, $Z^2$, R n and p are as defined in claim 1.

11. A mixture of claim 10, wherein, in formula (9), the rings A, B and C denote radicals of the formulae (1a), (1b) or (1c).

12. A mixture of claim 10, wherein, in formula (9), at least one bridge member $Z^1$ and $Z^2$ is a covalent bond.

13. A mixture of claim 1, wherein, in formula (1), the C atom of the end group of the formula H$_{2n}$XC$_n$[Y]$_p$, which carries the radical X, is separated from the ring A by not more than two C atoms of the end group chain.

14. A mixture of claim 11, wherein, in formula (1), halo is F or Cl.

15. In an electrooptical display element, based on a liquid crystal mixture, the improvement wherein the mixture is one of claim 1.

16. A mixture of claim 1, wherein n is 4–12.

* * * * *